US009124955B2

(12) United States Patent
Geva et al.

(10) Patent No.: US 9,124,955 B2
(45) Date of Patent: Sep. 1, 2015

(54) VEHICLE DRIVER MONITOR AND A METHOD FOR MONITORING A DRIVER

(75) Inventors: Nir Geva, Nes Ziona (IL); Yacov Geva, London (GB); Yair Tal, Matan (IL)

(73) Assignee: CARD GUARD SCIENTIFIC SURVIVAL LTD., Rehovot (IL)

( * ) Notice: Subject to any disclaimer, the term of this patent is extended or adjusted under 35 U.S.C. 154(b) by 606 days.

(21) Appl. No.: 13/235,523

(22) Filed: Sep. 19, 2011

(65) Prior Publication Data
US 2013/0070043 A1    Mar. 21, 2013

(51) Int. Cl.
| H04Q 9/00 | (2006.01) |
| A61B 5/18 | (2006.01) |
| B60K 28/06 | (2006.01) |
| G08B 21/06 | (2006.01) |
| G08B 21/22 | (2006.01) |
| G08B 21/24 | (2006.01) |
| G08B 25/01 | (2006.01) |
| A61B 5/00 | (2006.01) |
| A61B 5/0205 | (2006.01) |
| A61B 5/021 | (2006.01) |
| A61B 5/08 | (2006.01) |
| A61B 5/083 | (2006.01) |
| A61B 5/145 | (2006.01) |
| A61B 5/1455 | (2006.01) |
| A61B 5/16 | (2006.01) |
| H04N 7/14 | (2006.01) |

(52) U.S. Cl.
CPC ............... *H04Q 9/00* (2013.01); *A61B 5/0022* (2013.01); *A61B 5/18* (2013.01); *B60K 28/06* (2013.01); *B60K 28/066* (2013.01); *G08B 21/06* (2013.01); *A61B 5/021* (2013.01); *A61B 5/02055* (2013.01); *A61B 5/0816* (2013.01); *A61B 5/0836* (2013.01); *A61B 5/1455* (2013.01); *A61B 5/14532* (2013.01); *A61B 5/165* (2013.01); *A61B 5/4845* (2013.01); *A61B 5/6893* (2013.01); *A61B 5/747* (2013.01); *A61B 2560/0242* (2013.01); *G08B 21/22* (2013.01); *G08B 21/24* (2013.01); *G08B 25/016* (2013.01); *H04N 7/147* (2013.01); *H04Q 2209/40* (2013.01); *H04Q 2209/60* (2013.01); *H04Q 2209/823* (2013.01)

(58) Field of Classification Search
USPC .................. 379/88.11, 88.12, 185; 348/14.02
See application file for complete search history.

(56) References Cited

U.S. PATENT DOCUMENTS

| 7,633,383 | B2 * | 12/2009 | Dunsmoir et al. | 340/435 |
| 7,671,752 | B2 * | 3/2010 | Sofer | 340/576 |
| 8,527,213 | B2 * | 9/2013 | Kailas et al. | 702/32 |
| 2006/0155175 | A1 * | 7/2006 | Ogino et al. | 600/301 |
| 2011/0313259 | A1 * | 12/2011 | Hatakeyama et al. | 600/300 |

* cited by examiner

Primary Examiner — Amal Zenati
(74) Attorney, Agent, or Firm — Reches Patents

(57) ABSTRACT

A method and a monitor for monitoring a driver of a vehicle, the monitor includes: multiple sensors coupled to at least one vehicle element or integrated with at least one vehicle element; a processor for: receiving physiological information relating to the driver from the multiple sensors; detecting, based on the physiological information, a health problem of the driver, an awareness level of the driver and a stress level of the driver; determining a selected action to be performed based on the detection, wherein the action is selected from a list consisting of: establishing a call to a remote assistance site, transmitting the physiological information to a remote assistance site, generating an audio alert, and generating a visual alert; and assisting in a completion of the selected action.

48 Claims, 11 Drawing Sheets

FIG. 5    500

VEHICLE DRIVER MONITOR AND A METHOD FOR MONITORING A DRIVER

BACKGROUND OF THE INVENTION

Many car accidents occur due to driver's physical or mental condition, and especially due to the driver's stress, tiredness, or due to other medical problem.

There is a growing need to reduce car accidents, especially those that can be predicted in advance.

SUMMARY OF THE INVENTION

According to an embodiment of the invention a monitor for monitoring a driver of a vehicle is provided, the monitor may include: multiple sensors coupled to at least one vehicle element or integrated with at least one vehicle element; and a processor for: receiving physiological information relating to the driver from the multiple sensors; detecting, based on the physiological information, a health problem of the driver, an awareness level of the driver and a stress level of the driver; determining a selected action to be performed based on the detection, wherein the action is selected from a list consisting of: establishing a call to a remote assistance site, transmitting the physiological information to a remote assistance site, generating an audio alert, and generating a visual alert; and assisting in a completion of the selected action.

A method for monitoring a stress level of a driver of a vehicle can be provided, according to an embodiment of the invention and may include: receiving physiological information indicative of a stress level of the driver, from at least one sensor that is located within the vehicle and in a vicinity of the driver; detecting a stress level of the driver based on the physiological information, stored physiological information history and at least one predefined measurement threshold; determining, based on the stress level of the driver, whether to initiate a stress level reduction action; performing, based on the determination, the stress level reduction action while the driver is within the vehicle, wherein the stress level reduction action is selected out of playing a relaxing music and activating a neck or back massage.

A method for monitoring an awareness state of a driver, may include: receiving physiological information indicative of an awareness level of a driver, from at least one sensor that is located in a vicinity of a driver; detecting the awareness level of the driver based on the physiological information, stored physiological information history and predefined measurements thresholds; determining, based on the awareness level of the driver, whether to initiate an awaking action; performing, based on the determination, the awaking action while the driver is within the vehicle, wherein the awaking action is selected from a list consisting of: playing a music, playing a speech and playing a sound.

A method may be provided, according to an embodiment of the invention and may include: receiving physiological information relating to the driver from at least one sensor; detecting, based on the physiological information, a health problem of the driver, an awareness level of the driver and a stress level of the driver; determining a selected action to be performed based on the detection, wherein the action is selected from a list consisting of: establishing a call to a remote assistance site, transmitting the physiological information to a remote assistance site, generating an audio alert and generating a visual alert; and performing the selected action.

Any of the methods mentioned above can be executed by the monitor mentioned in the summary.

The monitor may include a wireless communication device for establishing a call to the remote assistance site and for transmitting the physiological information to the remote assistance site.

The monitor may include a storage module for storing a history of physiological information of the driver.

The monitor may include a display for displaying video during a video conference call between the driver and the remote assistance site; for displaying the visual alert; and for displaying visual content that is indicative of the physiological information.

The multiple sensors may be a one-lead ECG, a heart rate sensor, an oxygen saturation sensor, a blood pressure sensor, a body temperature sensor, and a breath sensor.

The monitor may include at least one ambient sensor out of an ultra violet sensor for reading an ultra violet radiation measurement and at least one gas sensor for reading at least one gas measurement.

The at least one gas sensor may be a nitrogen oxide gas sensor or a carbon dioxide gas sensor.

The processor may be configured to receive a gas measurements and to instruct a ventilation system of the vehicle to provide fresh air into the vehicle when a gas measurement indicates that a gas level exceeds a predefined gas level threshold.

The processor may be configured to receive ultra violet radiation measurements and to instruct a window controller of the vehicle to close a window of the vehicle when an ultra violet radiation measurement indicates that a level of ultra violet radiation exceeds a predefined ultra violet level threshold.

The generating of the audio alert may include playing music.

The generating of the audio alert may include playing a speech.

The processor is configured to detect a decreased awareness level of the driver and to determine an awaking action selected from a list consisting of: playing music, talking to the driver and activating a wake-up call.

The monitor may include an alcohol sensor for detecting an alcohol level in a blood of the driver; wherein the processor is configured to prevent an ignition of the vehicle if the alcohol level in the blood of the driver exceeds a predefined alcohol level threshold.

The monitor may include, may include a voice recognition sensor arranged to authenticate a driver that undergoes an alcohol level test.

The multiple sensors may include a one-lead ECG sensor, a heart rate sensor, an oxygen saturation sensor, a blood pressure sensor, a body temperature sensor, glucose meter, weight scale, environmental sensor and a breath sensor.

The multiple sensors may include a one-lead ECG that may include two electrodes coupled to the steering wheel; and wherein the display is configured to display an ECG graph when a one-lead ECG test is performed and to display a message that requires a confirmation to send one-lead ECG test results to the remote assistance site.

The vehicle elements coupled to one or more sensors can be a steering wheel of the vehicle or a seatbelt of the driver.

The monitor may include a smell detector arranged to detect a smell that differs from a predefined set of desired smells.

The selected action can include at least one of opening a window of the vehicle, closing a window of the vehicle, changing a parameter of an air conditioning system, allowing an automatic driver to assume control of the vehicle, and generating nerve stimulation.

The selected action may include generating nerve stimulation.

The method may include determining to initiate the stress level reduction action when a difference between at least one measurement of the physiological information and an average of associated stored measurements exceeds a predefined measurement change threshold.

The method may include determining to initiate the stress level reduction action if at least one measurement of the physiological information exceeds a corresponding predefined measurement threshold.

The method may include detecting, by a smell detector, a smell that differs from a predefined set of desired smells.

The stress level reduction may include at least one of changing a parameter of an air conditioning system, allowing an automatic driver to assume control of the vehicle, and generating nerve stimulation.

The method may include determining to initiate the awaking action when a difference between at least one measurement of the physiological information and an average of associated stored measurements exceeds a predefined measurement change threshold.

The method may include determining to initiate the awaking action if at least one measurement of the physiological information drops below a corresponding predefined measurement threshold.

The method may include, wherein the performing of the selected action may include establishing a call to the remote assistance site and transmitting the physiological information to the remote assistance site.

The method may include storing a history of the physiological information of the driver.

The performing of the selected action may include displaying video during a video conference call between the driver and the remote assistance site.

The performing of the selected action may include displaying the visual alert and displaying visual content that is indicative of the physiological information.

The method may include receiving gas measurements and instructing a ventilation system of the vehicle to provide fresh air into the vehicle when a gas measurement indicates that a gas level exceeds a predefined gas level threshold.

The method may include receiving ultra violet radiation measurements and instructing a window controller of the vehicle to close a window of the vehicle when an ultra violet radiation measurement indicates that a level of ultra violet radiation exceeds a predefined ultra violet level threshold.

The method may include playing music.

The method may include playing a speech.

The method may include, detecting a decreased awareness level of the driver and determining an awaking action selected from a list consisting of: playing music, talking to the driver and activating a wake-up call.

The method may include detecting an alcohol level in a blood of the driver and preventing an ignition of the vehicle if the alcohol level in the blood of the driver exceeds a predefined alcohol level threshold.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

Figure 1:
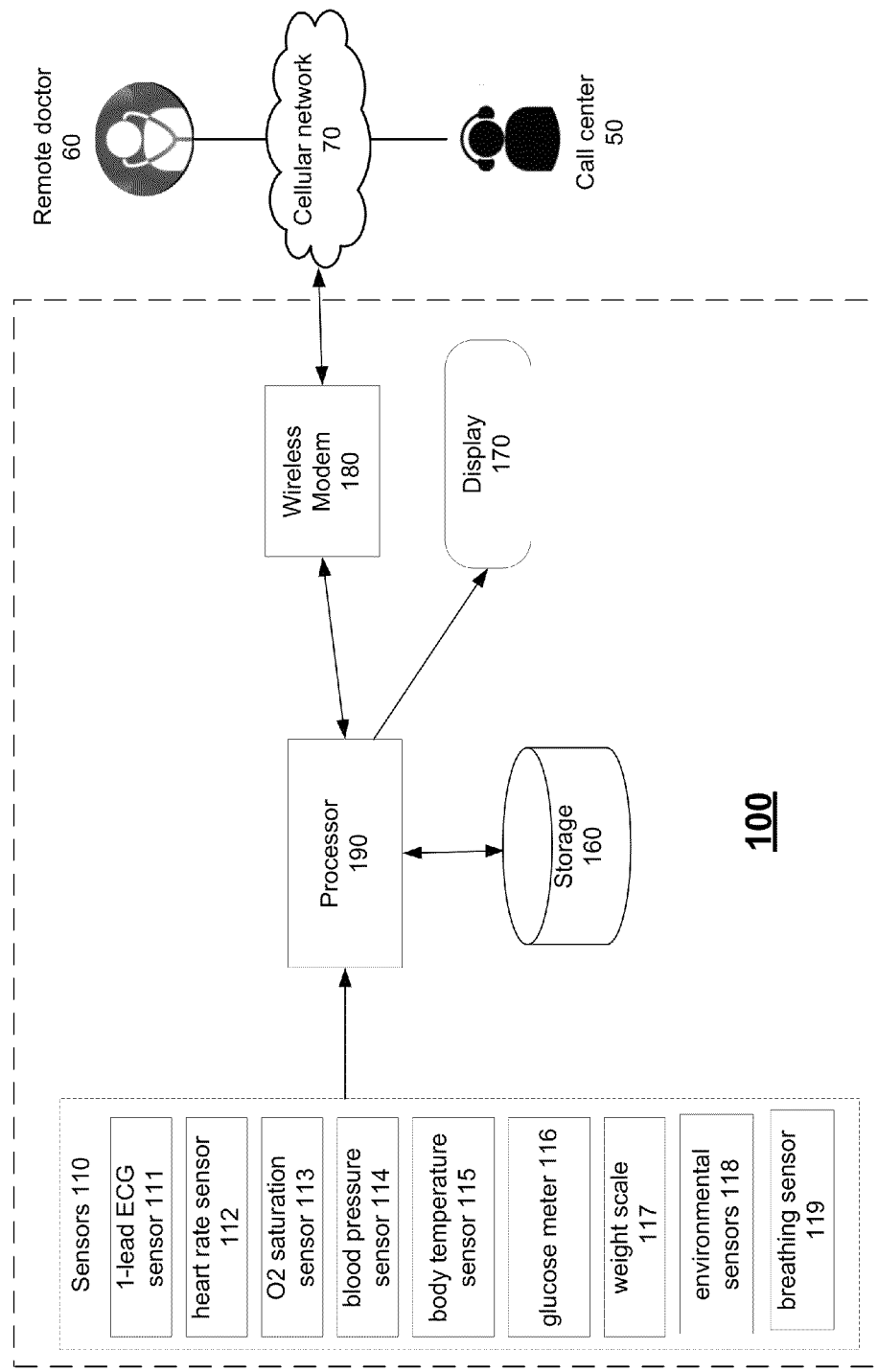
FIG. 1 is a block diagram of a vehicle driver monitor, according to an embodiment of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE PRESENT INVENTION

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

A vehicle driver monitor 100 is provided for monitoring a vehicle driver's physiological information and for detecting a safety and a health condition of the vehicle driver. A safety detection module of vehicle driver monitor 100 can perform awareness detection, stress detection, alcohol level detection or any other medical condition evaluation. The safety detection module 100 can take actions for awaking the driver in case that a sleepiness condition is detected and can take actions for relaxing the driver in case of stress detection. Upon detection of high level of alcohol, a vehicle ignition can be prevented. A health detection module of vehicle driver monitor 100 includes monitoring physiological information of the driver, such as vital signs, and communication with a remote assistance site in case of a health problem detection.

Vehicle driver monitor 100 monitors both the physical and mental condition of the driver, wherein the mental condition is related to awareness or stress of the driver and the physical condition is related to vital signs, such as but not limited to: heart rate, blood pressure, body temperature, Oxygen saturation, body temperature and the like. Vehicle driver monitor 100 can monitor ambient conditions that might affect the physical condition of the driver. The ambient conditions include air quality inside the vehicle that may be influenced by gasses that permeate the vehicle interior and UV radiation that can penetrate through a sun roof or a window. Vehicle driver monitor 100 can also monitor the alcohol level in the driver's blood.

Vehicle driver monitor 100 can take actions based upon each detected condition. For example: upon detecting a sleepiness condition, vehicle driver monitor 100 can alert the driver by activating audio alerts, music, speech, a third party wake-up call and the like. Upon detecting a medical condition, the system can call a remote assistance site, such as a health center or a remote doctor. Upon detecting an environmental problem, the system can reduce the environmental effect, by flowing fresh air into the vehicle, closing a sun roof and so on. According to another embodiment of the invention the vehicle driver monitor 100 can sense that a person or an animal was left (maybe forgotten) in a vehicle that may be shut down. This situation may be referred to as "leaving a person or animal in a closed vehicle" situation. The detection of such situation can include (a) sensing that a person or animal is left in the vehicle (using temperature sensors, movement detection of an entity within the vehicle, sound recognition, breathing recognition that may be sensed by detecting certain air movements within a closed vehicle, using a Ultra-WideBand radar to sense the presence of a person or animal in the vehicle, (b) sensing that the vehicle is shut down (sensing the state of the vehicle as being shut down can include sensing the lack of electricity in certain points of the vehicle, getting an indication from a vehicle computer, sensing that a key is not inserted into an ignition unit, sensing that the car is static for at least a predetermined amount of time). The detection (see stage 529 of FIG. 5) can trigger a selected action such as but not limited to opening a window of the vehicle, sending an audio alert, sending a message (over a communication network such as a short range network, a long range network, a cellular network, a wireless network) to a third entity (the driver, another person registered as having an interest in the vehicle, a car rental company, an emergency service provider and the like) that indicated of a potential leaving a person or animal in a closed vehicle" situation (see, for example, stage 551 of FIG. 5). The alert can be a SMS message but this is not necessarily so. It is noted that during a period during which the "leaving a person or animal in a closed vehicle" situation exists the type of alerts, magnitude of alerts, the frequency of alerts (amount of alerts per minute) may change. Especially, the magnitude of an audio alert can increase, the frequency of alerts can increase, the number of receivers that receive the alert can increase ass time goes by and the situation is not resolved. For example, relatively silent alerts (SMS messages) can change to audio messages (activating the alarm system of the vehicle) after predetermined periods. Yet for another example, a response to such a situation can include opening one or more windows of the vehicle to induce a flow of air in the vehicle.

The opening of a window can be regarded as an extreme response as it may expose the person or animal in the car to ambient rain, heat and the like and can increase the chances of stealing the vehicle. Thus—this step can be initiated only if the ambient temperatures are within a predefined range (for example 10-30 degrees), at least a predefined period from the detection of the situation has lapsed (for example—at least 10 or 15 minutes), there is no rain or snow, and the like. The windows can be slightly opened, partially opened or completely opened. The amount of opening can be determined based on a predefined schedule or based upon a response of the person or animal in the vehicle to the opening attempt. If the heart rate of a person within the vehicle is too low and the partial opening of the window does not increase the hear rate to be within a desired range then the window can be further opened. If, opening a window causes the heart rate to increase to an undesired level the window can be partially closed.

Vehicle driver monitor 100 can display the detected condition to the driver and allow him to decide of a way of action.

FIG. 1 is a block diagram illustrating vehicle driver monitor 100 that includes a processor 190 for: (i) receiving physiological information from multiple sensors 110; (ii) detecting a health problem of the vehicle driver, an awareness of the vehicle driver and a stress of the vehicle driver; (iii) determining an action to be taken when the health problem, the awareness or the stress is detected. Processor 190 is connected to multiple sensors, collectively denoted 110, such as but not limited to: a 1-lead ECG detector 111, a heart rate sensor 112, an Oxygen (O2) saturation sensor 113, a blood pressure sensor 114, a body temperature sensor 115, a glucose meter 116, a weight scale 117, environmental sensors 118 and breathing sensor 119. The glucose meter 116 can be embedded in the vehicle (for example in the steering wheel) and the weight scale 117 can be connected to the driver seat or to any other seat. The sensors can also include a radar (such as a UWB radar), a camera and the like. The radar can be located at the ceiling of the vehicle, in front of the driver, above the driver, connected to a seatbelt, and the like. UWB signals transmitted from the radar at a high repetition rate (for example—at least 200 UWB pulses per second) can be emitted towards the driver (or have at least a part of the radiation reach the driver), and once emitted back can be analyzed (for example by using Doppler effect analysis) to determined the heart rate, breathing rate, blood pressure, and the like. In case of accident the UWB pulses can be processed to detect fluid in the lungs of the driver, and the like. The accident can be detected by monitoring the speed and/or acceleration of the vehicle. A sudden change in the vehicle speed that is followed by a lack of movement can indicate that an accident occurred—especially if the monitored persons do not exit the car for a predetermined period (minute, few minutes) after the vehicle stops.

Some of multiple sensors 110 can be coupled to the steering wheel, such as sensors that can read vital signs from a touch of a driver hand, for example: heart rate sensor 112, O2 saturation sensor 113, a blood pressure sensor 114 and body temperature sensor 115. Multiple sensors 110 can be attached to the steering wheel or embedded within the steering wheel. One-Lead ECG detector 111 includes 2 electrodes on the steering wheel.

Some of multiple sensors 110 can be attached to a seatbelt or embedded in the seatbelt, for example: heart rate sensor 112, body temperature sensor 115 and breathing sensor 119. The sensors can be Environmental sensors 118 can be attached or embedded in any part of the vehicle's interior. For example, environmental sensors 118 can include a UV sensor that is attached to a window or a sun-roof of the vehicle. Environmental sensors 118 can include a gas sensor that is attached to the front panel of the vehicle or anywhere else in the vicinity of the driver. The gas sensor detects gas presence such as: NOx (nitrogen oxides gas) and $CO_2$ (carbon dioxide gas).

Processor 190 is coupled to a wireless modem 180 or any other cellular or wireless communication device. Wireless modem 180 is configured to establish an audio and/or a video call with a remote assistance site, such as a health center 50 (also referred to as a call center) or a remote doctor 60 via a wireless network such as cellular network 70. Wireless modem 180 is also configured to send monitored data, such as ECG record, to health center 50 or remote doctor 60.

Vehicle driver monitor 100 includes a display 170 for displaying a video during a video call and for displaying physiological measurements, such as ECG graph, heart pulse, Oxygen level, blood pressure, body temperature, glucose level, body weight, gas measurements, UV level, breath rate, and so on.

Vehicle driver monitor 100 may further include a storage module 160 for storing a history of physiological information and for temporal buffering of test results prior to sending them to health center 50. The stored physiological information history can be used for learning the normal level of the driver's vital signs and for detecting irregular conditions of the driver. For example: a driver whose normal heart rate is averaged around 60 BPM (according to heart rate results that are stored in storage 160) is suddenly detected with a 90 BPM pulse. Although a 90 BPM is medically considered as a normal pulse that does not require any treatment, it might signal a stress condition of this specific driver. As for another example: a driver, whose normal breath rate is averaged around 20 breaths per minute, is detected with a 12 breaths per minute may be sleepy.

Figure 6:
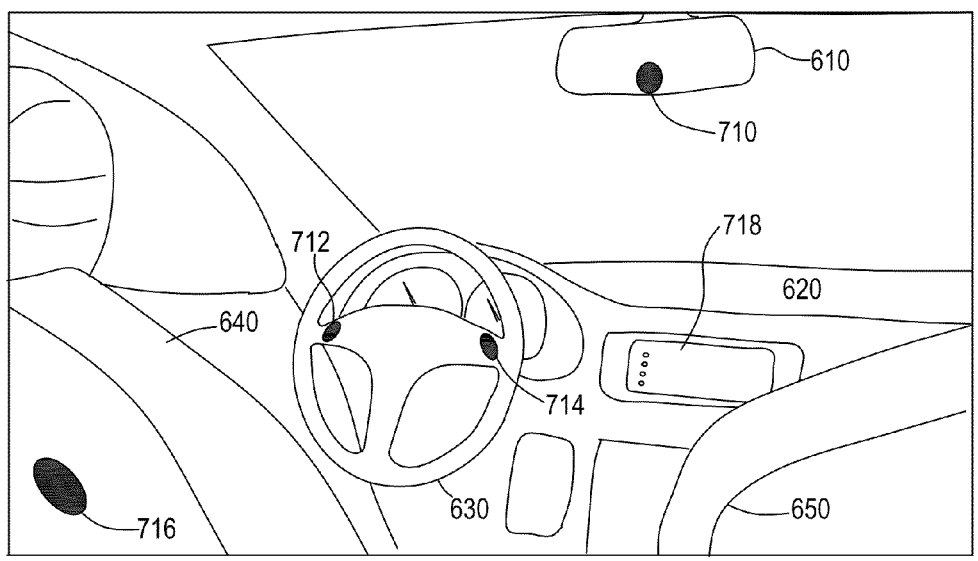
FIG. 6 illustrates various sensors that are located within a vehicle according to an embodiment of the invention.
Figure 7:
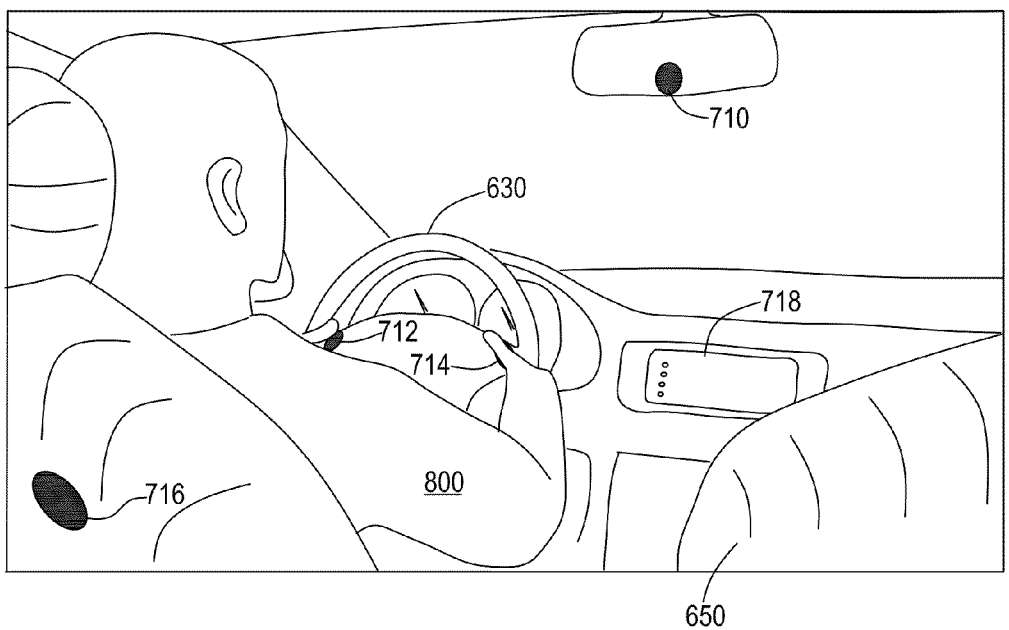
FIG. 7 illustrates a driver and various sensors that are located within a vehicle according to an embodiment of the invention.
Figure 8:
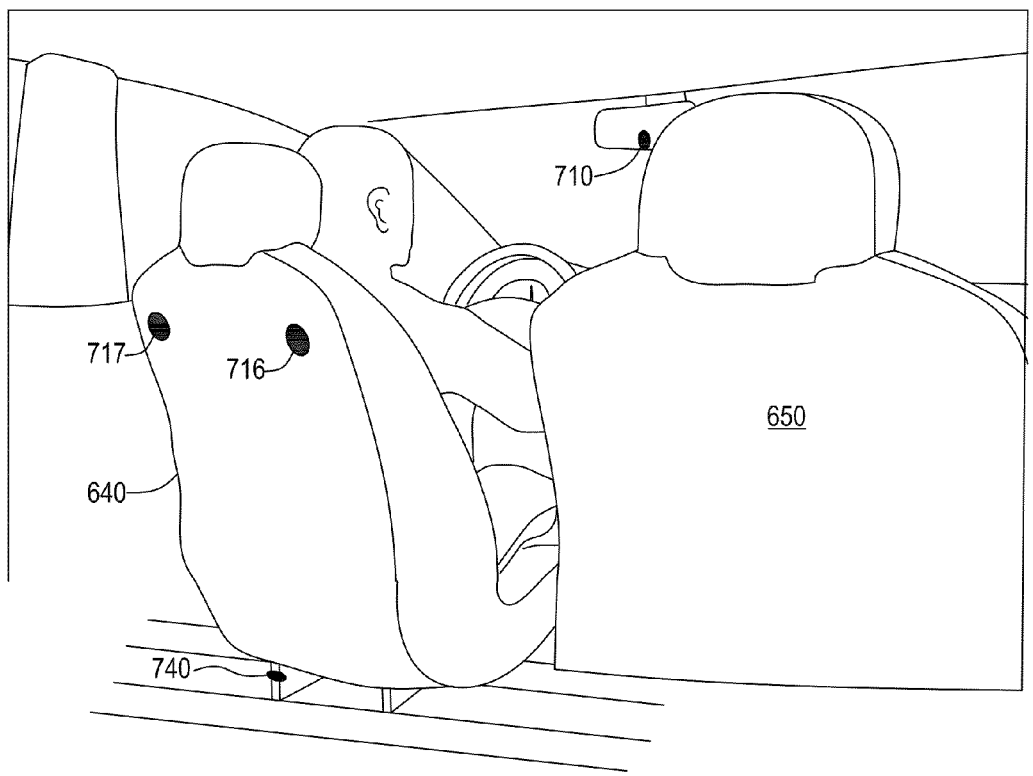
FIG. 8 illustrates a driver and various sensors that are located within a vehicle according to an embodiment of the invention.
Figure 9:
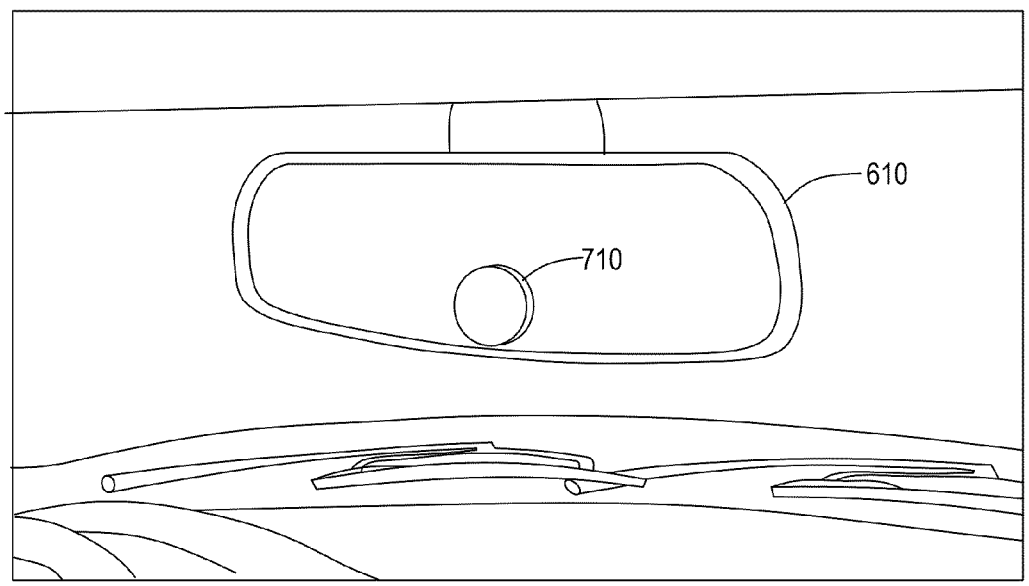
FIG. 9 illustrates a camera that is located within a vehicle according to an embodiment of the invention.

FIG. 6 illustrates various sensors 710, 712, 714 and 716 that are located within a vehicle according to an embodiment of the invention. FIG. 7 illustrates a driver 800 and various sensors 710, 712, 714 and 716 that are located within a vehicle according to an embodiment of the invention. FIG. 8 illustrates a driver 800 and various sensors 710, 716, 717 and 740 that are located within a vehicle according to an embodiment of the invention. FIG. 9 illustrates a camera 710 that is located within a vehicle according to an embodiment of the invention.

Figure 11:
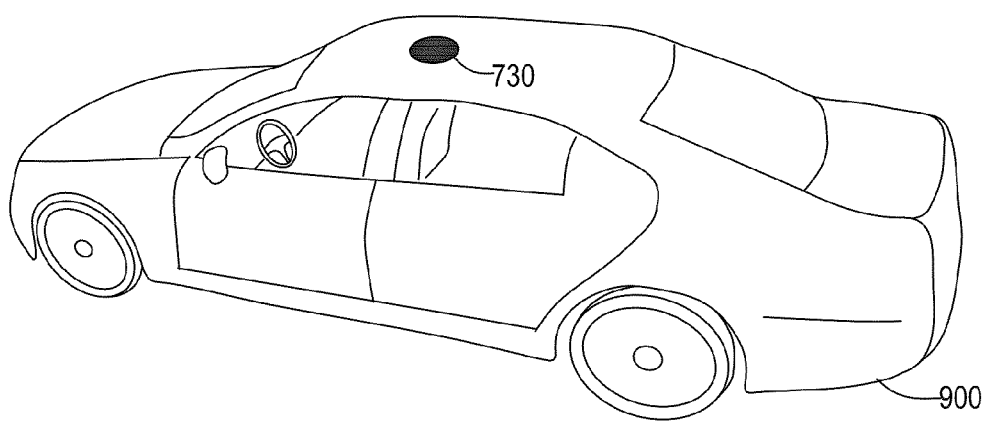
FIG. 11 illustrates a radar that is located within a vehicle according to an embodiment of the invention.

FIG. 11 illustrates a radar 730 that is located within a vehicle according to an embodiment of the invention. Camera 710 is illustrated as being connected to the drivers mirror 610. The camera 710 is sensor and can be directed towards the driver or any other area of the vehicle. Steering wheel 630 is illustrated as including two sensors 712 and 714 that are located in opposite sides of the steering wheel, facing the driver 800 and located near the areas of the steering wheel that are expected to be contacted by the driver 800.

Dashboard 620 may include a display 718. Environmental sensors 716 and 717 are located at the rear facet of the driver seat 640. Radar 730 is located within the vehicle, at the center of the vehicle interior space and above the driver 800 and any other passengers. The radar can be located on other locations but coupling it to the ceiling of the vehicle may provide is a relatively undisturbed field f view. It is noted that the radar 720 can be located at the front portion of the vehicle—between the driver seat and the front window and may directly face the driver. The vehicle can include one or more radars and multiple radars can be allocated per person and may operate in different frequencies, different times, different codes to reduce mutual interference. Any sensors of FIGS. 6-11 can be equivalent to the sensors of FIG. 1. Especially, sensors 716 and 717 can be equivalent to environmental sensors 118 of FIG. 1. Sensors 712 and 716 can be equivalent to sensors 111,112,113,114,115,116 and 119 of FIG. 1. Sensors 112 and 119 can be implemented by radar 730, sensors 716, 717, 712, 714 and 710. Weight scale can be implemented by sensor 740.

Figure 2:
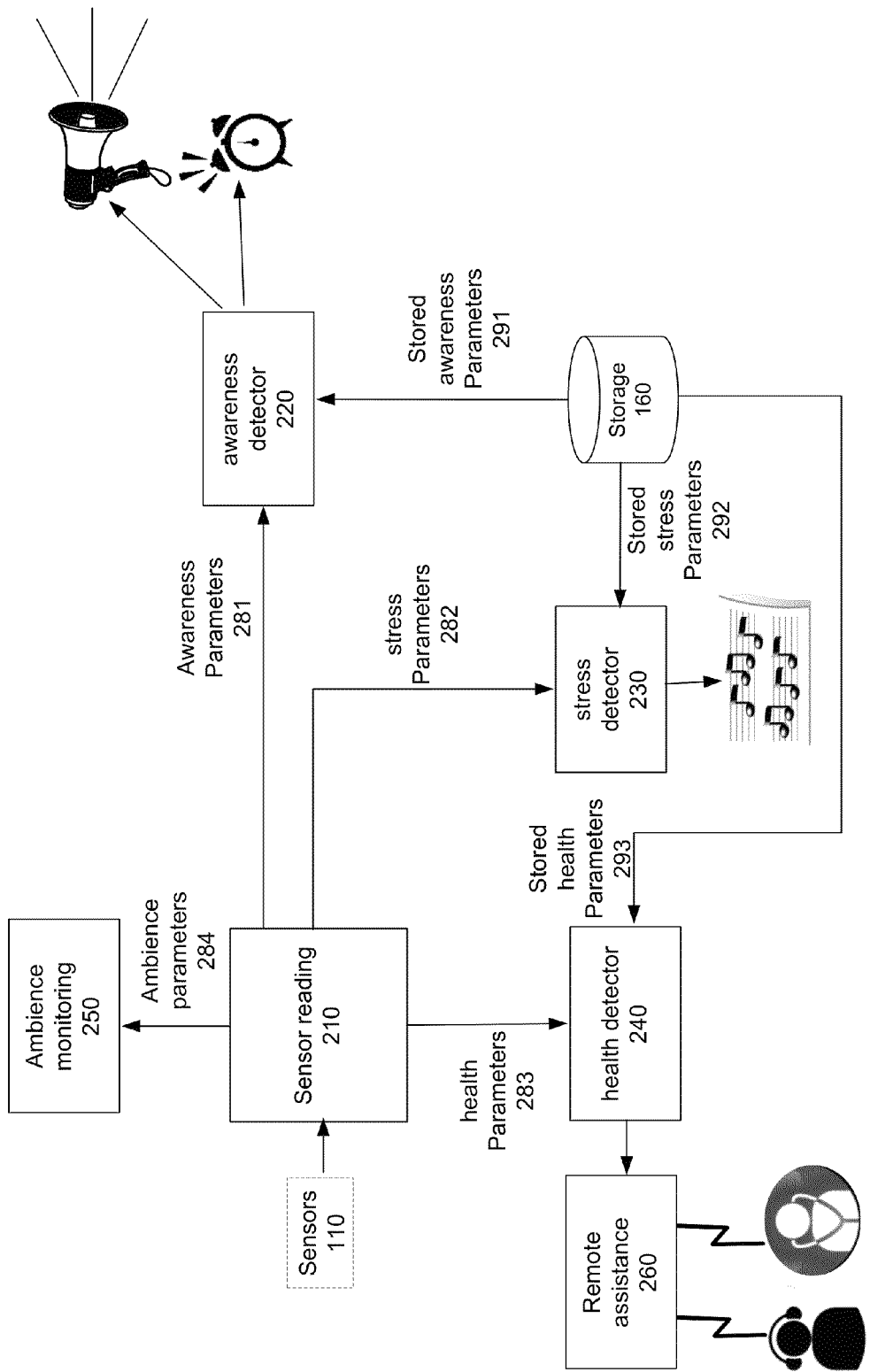
FIG. 2 is a functional block diagram of a vehicle driver monitor, according to an embodiment of the invention.

FIG. 2 is a functional block diagram of Vehicle driver monitor 100. Awareness detector 220 continuously monitors the driver's awareness by periodically receiving awareness measurements 281 from a sensor reading 210 and comparing awareness measurements 281 to predefined awareness measurement thresholds. Additionally or alternatively, awareness detector 220 can compare at least one measurement of awareness measurements 281 to an average of at least one of stored awareness measurements 291, retrieved from storage 160.

Awareness measurements 281 can include measurements, such as breath rate, heart rate, blood pressure and the like. If, for example, a breath rate measures 12 breaths per minute and an average of the stored breath measurements is 20 breaths per minute, a sleepiness condition might be determined. The sleepiness condition might be determined according to one of awareness measurements 281, such as breaths per minute or according to a combination of multiple measurements out of awareness measurements 281. According to another embodiment, the sleepiness condition can be determined if an awareness measurement, e.g. the number of breaths per minute, drops below a predefined awareness measurement threshold.

If awareness detector 220 identifies a sleepiness condition, it can alert the driver by: (i) talking to him; (ii) playing music; (iii) using a 3rd party wake up call, (iv) generating a relatively low amplitude nerve stimulation (for example—AC current of few miliAmperes) that can be sensed by the driver while not shocking the driver), (v) changing a parameter (flow, temperature) of air that is circulated in the vehicle or directed towards the driver.

Stress detector 230 continuously monitors the driver's stress by periodically receiving stress measurements 282 from sensor reading 210 and comparing stress measurements 282 to predefined stress measurement thresholds. Additionally or alternatively, stress detector 230 can compare at least one measurement of stress measurements 282 to an average of at least one of stored stress measurements 292, retrieved from storage 160. Stress measurements 282 can include measurements, such as breath rate, heart rate, blood pressure and the like. If, for example, heart rate measures 100 beats per minute and an average of the stored heart rate measurements is 60 beats per minute, a stress condition might be determined. The stress condition might be determined according to one of stress measurements 282, such as heart rate measurement or according to a combination of multiple measurements out of stress measurements 282. According to another embodiment, the stress condition can be determined if a stress measurement, e.g. number of heart beats per minute, exceeds a predefined stress measurement threshold.

If stress detector 230 identifies a stress state then stress detector 230 will suggest the driver several options for relaxing. (Relaxing music, back or neck massage, and so on). Display 170 can display the current stress level of the driver.

A health care module 240 can receive health measurements 283 from sensor reading 210, including measurements such as: One-Lead ECG, Heart rate, O2 saturation, Blood pressure, body temperature, Glucose meter, weight scale, environmental sensors and breathing sensor.

One-Lead ECG test is performed using the 2 electrodes on the steering wheel. Once the test is done a message will be displayed on display 170 that notify the driver that the ECG test is being performed and asking the driver whether to transmit the ECG test to health center 50. Optionally, the ECG graph is displayed on display 170.

The heart rate sensor measures the driver's heart beat. Once the test is done, the test result will be displayed on display 170.

The oxygen saturation sensor measures the driver's oxygen saturation in the blood and the heart rate. Once test is done, the test result will be displayed on display 170, showing the oxygen saturation percentage and the heart rate.

The blood pressure detector measures the driver's blood pressure. Once the test is done, the test result will be displayed on display 170, showing the systolic and diastolic measures along with the heart rate.

The body temperature detector measures the driver's body temperature. Once the test is done, the body temperature will be displayed on display 170.

The glucose detector measures the driver's level of blood glucose. Once the test is done, the glucose level will be displayed on display 170. The glucose detector (glucose sensor) can require a drop of blood of the driver but may be a wireless glucose detector such as the wireless Glucose detectors of Glucon Medical, Israel. The Glucose sensor can be integrated to the vehicle (for example can be integrated with the steering wheel, or not. It can, for example, be located I the glove compartment and be taken from the glove compartment only when needed.

The weight detector measures the driver's body weight and can be coupled to the driver's seat. Once the test is done, the weight will be displayed on the screen.

An ambience monitoring 250 receives ambience measurements 284 from sensor reading 210 that include ambience measurements such as an air quality measurement and a UV measurement. The air quality monitor continuously monitors gasses inside the vehicle. If one of the monitored gasses exceeds a predefined gas measurement threshold processor 190 may instruct a ventilation system of the vehicle to flow fresh air into the vehicle and the gas measurements will be displayed on display 170.

The UV sensor may be attached to a convertible or the sunroof open. If the UV measurement exceeds a predefined UV measurement threshold, the UV level will be displayed on display 170 and processor 190 may instruct a window controller to close a window or a sun roof.

A breath sensor is embedded on the safety belt and counts the driver's number of breaths. The result of breaths per minute will be displayed on display 170.

A remote assistant 260 is activated upon detecting a health problem by health detector 240 and can connect the driver to health center 50 or to remote doctor 60. In case of emergency or personal safety condition, the driver can initiate a call to health center 50 or to remote doctor 60 by one touch for immediate assistance on a video conference or audio call.

The driver can navigate through a menu and view his/her personal data stored in storage 160 (history measurements and current measurements) on display 170.

An alcohol detector measures the driver's level of alcohol. According to one embodiment of the invention, an alcohol level sensor is embedded in the vehicle's key. In order to activate the key the driver has to exhale on it. In case the level of alcohol is above normal, the key won't activate an engine ignition.

Figure 10:
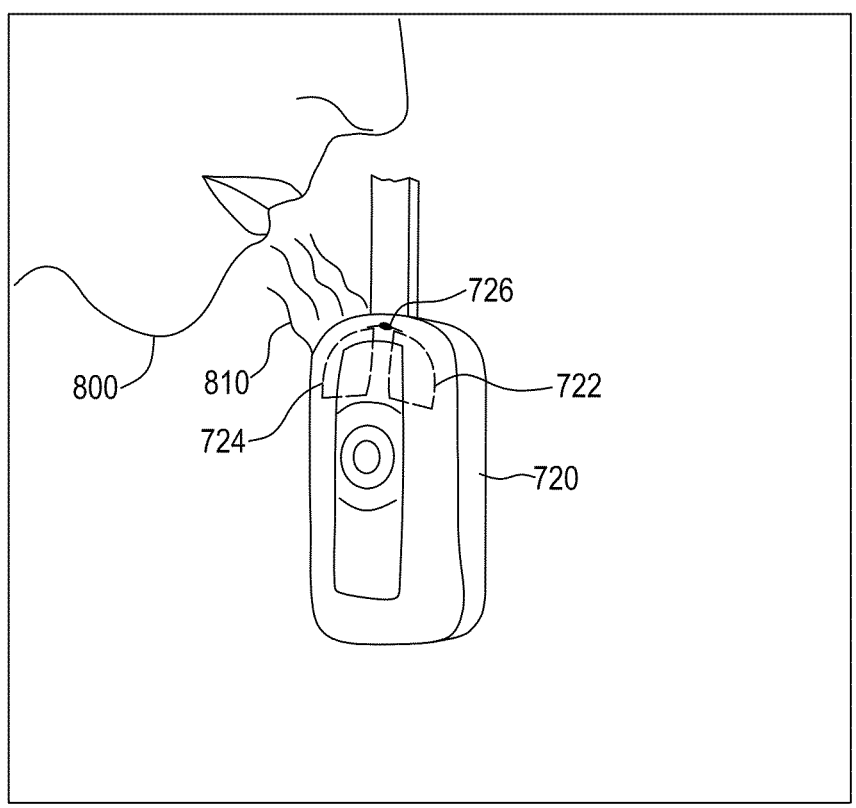
FIG. 10 illustrates a driver, an alcohol sensor and a voice recognition unit according to an embodiment of the invention.

In order to prevent a bypassing of the alcohol detector by a person that is not the driver the alcohol test can be accompanied by a voice recognition test (executed by a voice recognition sensor) that includes authenticating the driver during the alcohol analysis as the person (that is required to talk during the alcohol level test period) of whose breath is analyzed for detection of alcohol residues. Thus, the driver can be requested to say one or more words and the key can be activated only if the driver is authenticated and the alcohol level is below a predefined level. FIG. 10 illustrates a driver 800 that breaths towards an ignition key module 720 that includes an alcohol sensor 724 and a voice recognition module 722 that is coupled to a microphone 726. The microphone is proximate to a hole or aperture during which the alcohol sensor 724 samples the breath of the driver.

Figure 3:
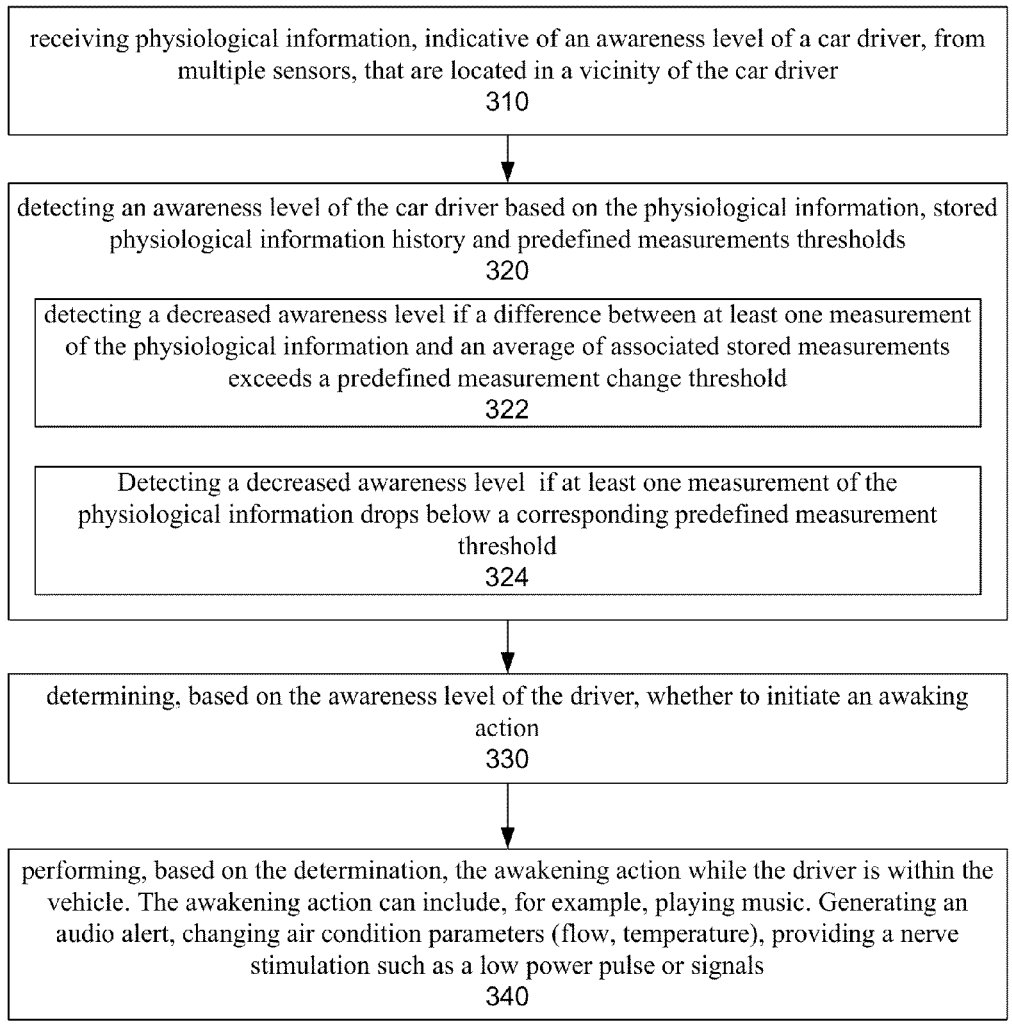
FIG. 3 is a flowchart of a method for monitoring an awareness of a driver.

FIG. 3 illustrates a method 300 for monitoring an awareness of a vehicle driver. Method 300 starts with a stage 310 of receiving physiological information, indicative of an awareness level of a vehicle driver, from multiple sensors, that are located in a vicinity of the vehicle driver. The physiological information may include: breath rate, heart rate, blood pressure and any other measurement that might indicate a decreased awareness of the vehicle driver. The multiple sensors may include: heart rate sensor 112, blood pressure sensor 114, breathing sensor 119 or any other sensor that can measure a physiological parameter that is indicative of awareness. Each sensor out of the multiple sensors may be either attached to the seatbelt of the driver, to any other seatbelt, attached to the steering wheel, embedded in the seatbelt or embedded in the steering wheel or located anywhere within the vehicle.

Stage 310 is followed by stage 320 of detecting the awareness level of the vehicle driver based on the physiological information, stored physiological information history and predefined measurements thresholds.

Stage 320 may include stage 322 of detecting a decreased awareness level if a difference between at least one measurement of the physiological information and an average of associated stored measurements exceeds a predefined measurement change threshold. For example, if a measurement of the breaths per minute drops by a predefined percentage or amount, comparing to an average of breaths per minute measurements, stored in storage 160, then a sleepiness condition may be detected. The predefined measurement change threshold can be an absolute number (e.g. a change of 8 breaths per minute) or it can be a percentage (e.g. a 30% change). A decreased awareness level can be detected if measurements related to more than one measurement type drop below an average of associated measurements, e.g. both breaths per minute and heart rate are dropped below the average breath rate of the driver.

Stage 320 may include stage 324 of detecting a decreased awareness level if at least one measurement of the physiological information drops below a corresponding predefined measurement threshold.

Stage 320 is followed by stage 330 of determining, based on the awareness level of the driver, whether to initiate an awaking action.

Stage 330 is followed by stage 340 of performing, based on the determination, the awakening action while the driver is within the vehicle. The awakening action can be playing a music, a speech or any other sound, generating a nerve stimulation.

Figure 4:
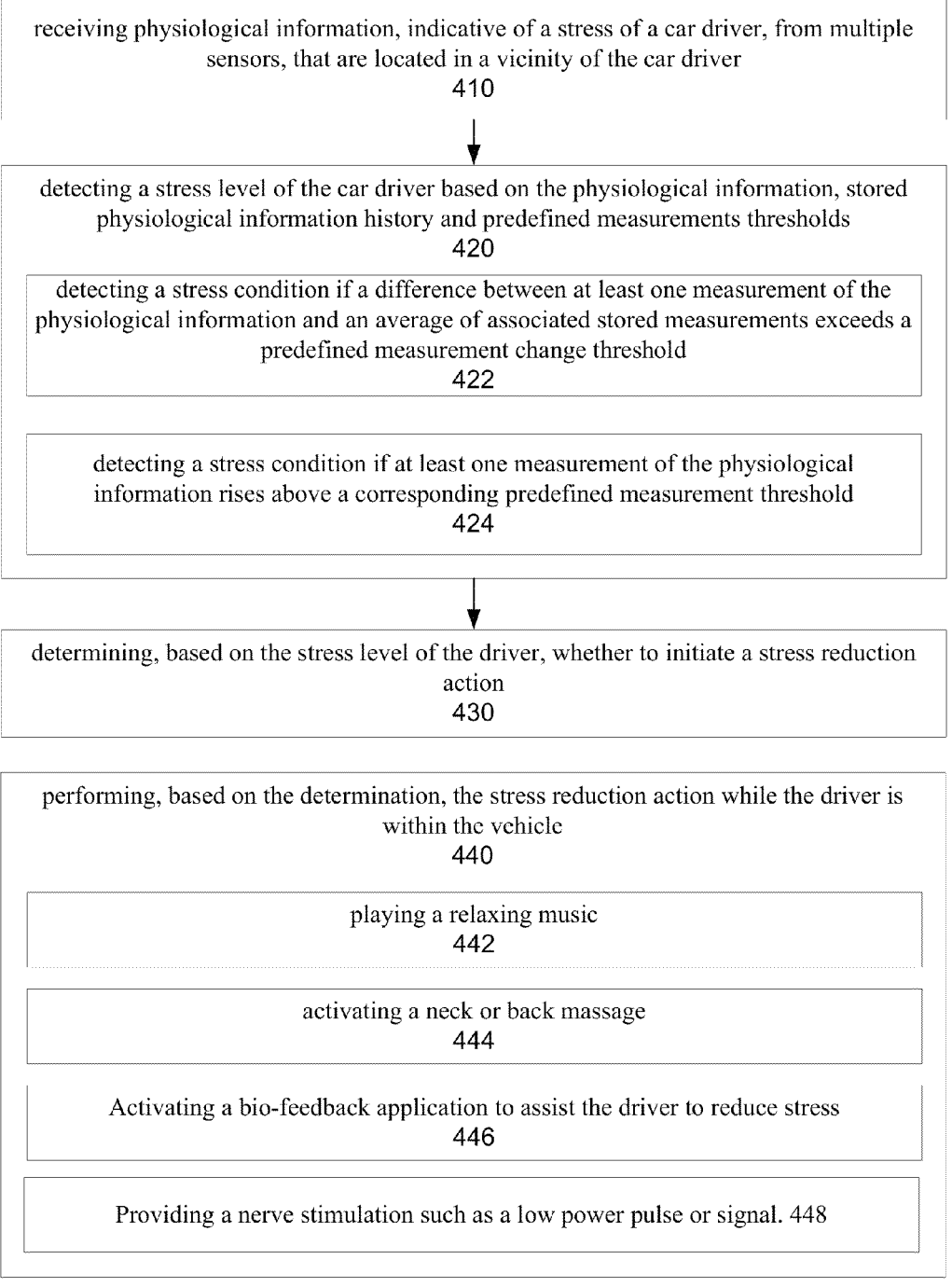
FIG. 4 is a flowchart of a method for monitoring a stress of a driver.

FIG. 4 illustrates a method 400 for monitoring a stress level of a vehicle driver. Method 400 starts with a stage 410 of receiving physiological information, indicative of a stress level of a vehicle driver, from multiple sensors, that are located in a vicinity of the vehicle driver. The physiological information may include: breath rate, heart rate, blood pressure and any other measurement that might indicate a stress condition of the vehicle driver. The multiple sensors may include: heart rate sensor 112, blood pressure sensor 114, breathing sensor 119 or any other sensor that can measure a physiological parameter that is indicative of stress. Each sensor out of the multiple sensors may be either attached to the seatbelt of the driver, attached to the steering wheel, embedded in the seatbelt or embedded in the steering wheel or located elsewhere within the vehicle. It is noted that one or more person that is not the driver can also be monitored and if its health condition is outside a desired health condition value then a response can be triggered. Various responses (selected actions) are illustrated, for example, in box 540 of FIG. 5.

Stage 410 is followed by stage 420 of detecting a stress level of the vehicle driver based on the physiological information, based on stored physiological information history and predefined measurements thresholds.

Stage 420 may include stage 422 of detecting a stress condition if a difference between at least one measurement of the physiological information and an average of associated stored measurements exceeds a predefined measurement change threshold. For example, if a measurement of the heart rate rises by a predefined percentage or amount comparing to an average of measurements of heart rate, stored in storage 160, then a stress condition may be detected. The predefined measurement change threshold can be an absolute number (e.g. a change of 30 BPM) or it can be a percentage (e.g. a 50% change). Stress condition can be detected if measurements related to more than one measurement type, rise above an average of associated measurements, e.g. both breaths per minute and heart rate rises above the average calculated to the driver.

Stage 420 may include stage 424 of detecting a stress condition if at least one measurement of the physiological information exceeds a corresponding predefined measurement threshold.

Stage 420 is followed by stage 430 of determining, based on the stress level of the driver, whether to initiate a stress reduction action.

Stage 430 is followed by stage 440 of performing, based on the determination, the stress reduction action while the driver is within the vehicle.

Stage 440 may include stage 442 of playing a relaxing music, stage 444 of activating a neck or back massage, stage 446 of activating a bio-feedback application to assist the driver to reduce stress, stage 448 of providing a nerve stimulation such as a low power pulse or signal, or a combination thereof. The stimulation can be applied through one or more electrodes embedded in the steering wheel, in the seatbelt or in the seat of the driver.

Figure 5:
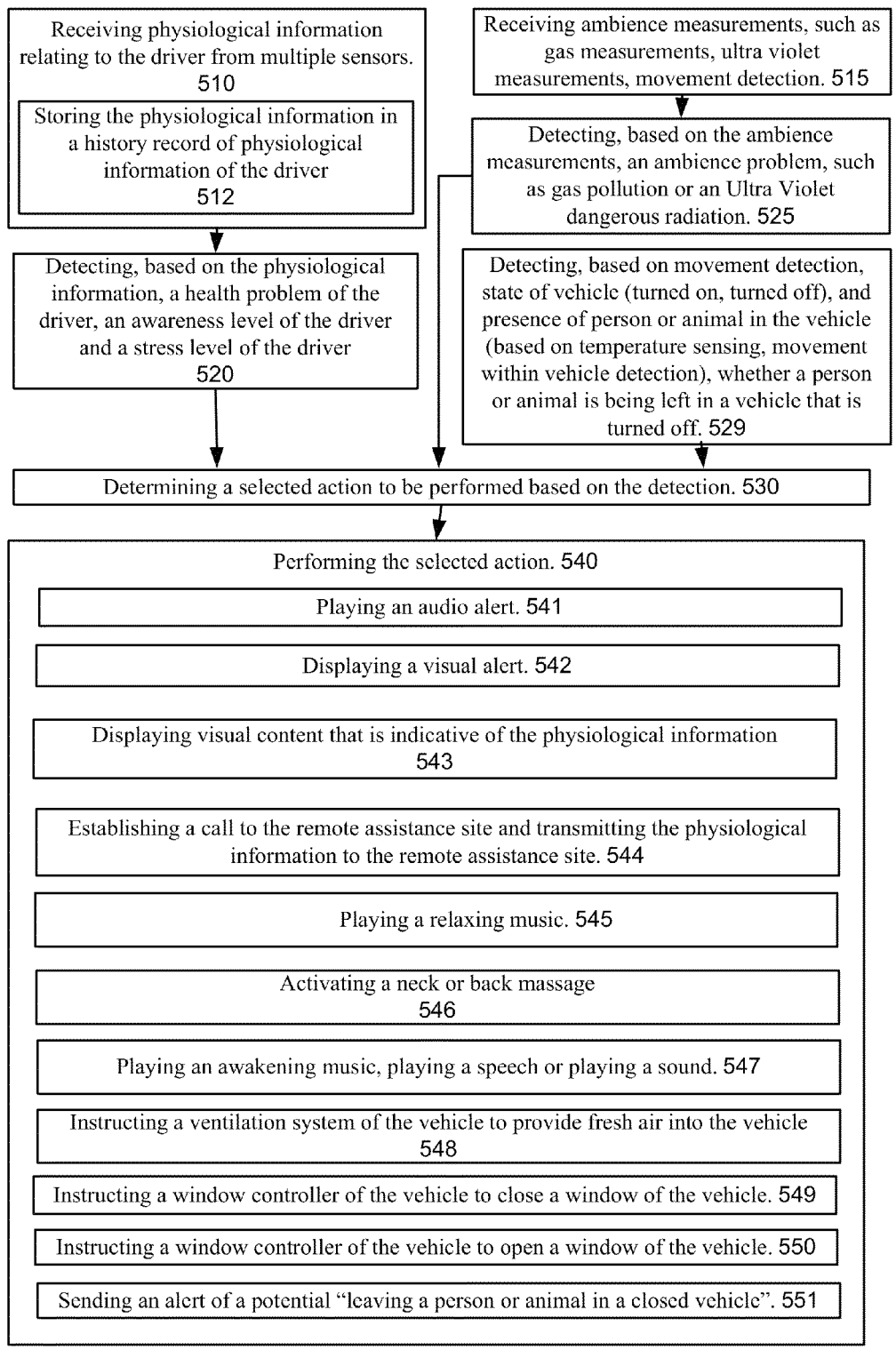
FIG. 5 is a flowchart of a method for monitoring a driver.

FIG. 5 illustrates a method 500 for monitoring a driver of a vehicle. Method 500 starts with a stage 510 of receiving physiological information relating to the driver from multiple sensors. The physiological information may include: Oxygen level, blood pressure, body temperature, glucose level, body weight, breath rate and any other measurement that might indicate a health problem, a stress level and an awareness level of the vehicle driver. The multiple sensors may include: heart rate sensor 112, an Oxygen (O2) saturation sensor 113, blood pressure sensor 114, a body temperature sensor 115, a glucose meter 116, a weight scale 117, breathing sensor 119 or any other sensor that can measure a physiological parameter that is indicative of a health problem, stress or awareness. Each sensor out of the multiple sensors may be either attached to the seatbelt of the driver, attached to the steering wheel, embedded in the seatbelt or embedded in the steering wheel or located elsewhere within the vehicle. It is noted that one or more person that is not the driver can also be monitored and if its health condition is outside a desired health condition value then a response can be triggered. Various responses (selected actions) are illustrated, for example, in box 540 of FIG. 5.

Stage 510 may include stage 512 of storing the physiological information in a history record of physiological information of the driver.

Method 500 may include stage 515 of receiving ambience measurements, such as gas measurements and ultra violet measurements.

Stage 510 is followed by stage 520 of detecting, based on the physiological information, a health problem of the driver, an awareness level of the driver and a stress level of the driver.

Stage 515 is followed by stage 525 of detecting, based on the ambience measurements, an ambience problem, such as gas pollution or an Ultra Violet dangerous radiation.

Stage 520 and stage 525 are followed by stage 530 of determining a selected action to be performed based on the detection.

Stage 530 is followed by stage 540 of performing the selected action. In case of health problem detection, stage 540 may include: stage 541 of playing an audio alert; stage 542 of displaying a visual alert; stage 543 of displaying visual content that is indicative of the physiological information; stage 544 of establishing a call to the remote assistance site and transmitting the physiological information to the remote assistance site. The call may be a video conference call and a video related to the call participants may be displayed on display 170.

In case of stress detection, stage 540 may include: stage 545 of playing a relaxing music; and stage 546 of activating a neck or back massage.

In case of awareness reduction detection, stage 540 may include: stage 547 of playing an awakening music, playing a speech or playing a sound.

In case of an ambience problem, stage 540 may include: stage 548 of instructing a ventilation system of the vehicle to provide fresh air into the vehicle when a gas measurement indicates that a gas level exceeds a predefined gas level threshold; and stage 549 of instructing a window controller of the vehicle to close a window of the vehicle when an ultra violet radiation measurement indicates that a level of ultra violet radiation exceeds a predefined ultra violet level threshold.

Stage 540 can include at least one of the following, when detecting a "leaving a person or animal in a closed vehicle" situation, stage 550 of instructing a window controller of the vehicle to open a window of the vehicle, and additionally or alternatively, stage 551 of sending an alert of a potential "leaving a person or animal in a closed vehicle".

According to an embodiment of the invention once an accident occurs various sensors in the vehicle can monitor the state of the persons in the vehicle and send information (physiological information) to a third party. Information obtained by multiple sensors can be correlated to provide more accurate information. For example, breathing can be sensed by a UWB radar, by sensing CO2 levels in the vehicle, by sensing movements and the like.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

We claim:

1. A monitor for monitoring a driver of a vehicle, the monitor comprises:
    multiple sensors coupled to at least one vehicle element or integrated with at least one vehicle element;
    a processor for:
        receiving physiological information relating to the driver from the multiple sensors;
        detecting, based on the physiological information, a health problem of the driver, an awareness level of the driver and a stress level of the driver; wherein the detecting of the health problem of the driver differs from measuring an alcohol level in a blood of the driver;
        determining a selected action to be performed based on the detection, wherein the action is selected from a list consisting of: establishing a call to a remote assistance site, transmitting the physiological information to a remote assistance site, generating an audio alert, and generating a visual alert; and assisting in a completion of the selected action;
wherein at least one of the following is held true:
(a) the monitor further comprises an ultra violet sensor for reading an ultra violet radiation measurement;
(b) the monitor further comprises at least one gas sensor that is selected from a nitrogen oxide gas sensor and a carbon dioxide gas sensor;
(c) the monitor further comprises an alcohol sensor and a voice recognition sensor; wherein the alcohol sensor is for detecting an alcohol level in the blood of the driver; wherein the processor is configured to prevent an ignition of the vehicle if the alcohol level in the blood of the driver exceeds a predefined alcohol level threshold; wherein the voice recognition sensor is arranged to authenticate the driver that undergoes an alcohol level test;
(d) the monitor is arranged to detect a "leaving a person or an animal in a closed vehicle" situation and trigger a selected action selected out of an opening of a window of the vehicle, sending an audio alert, sending a message to a third entity that indicates of a potential "leaving a person or animal in a closed vehicle" situation;
(e) the monitor further comprises a radar arranged to monitor the driver and to provide an indication, in case of an accident, of fluid in lungs of the driver.

2. The monitor according to claim 1, further comprising a wireless communication device for establishing a call to the remote assistance site and for transmitting the physiological information to the remote assistance site.

3. The monitor according to claim 1, further comprising a storage module for storing a history of physiological information of the driver.

4. The monitor according to claim 1, further comprising a display for displaying video during a video conference call between the driver and the remote assistance site; for displaying the visual alert; and for displaying visual content that is indicative of the physiological information.

5. The monitor according to claim 1, wherein the multiple sensors are selected from a list consisting of: a one-lead ECG, a heart rate sensor, an oxygen saturation sensor, a blood pressure sensor, a body temperature sensor, and a breath sensor.

6. The monitor according to claim 1, further comprising the ultra violet sensor for reading the ultra violet radiation measurement.

7. The monitor according to claim 1 comprising the at least one gas sensor that is selected from the nitrogen oxide gas sensor and the carbon dioxide gas sensor.

8. The monitor according to claim 7, wherein the processor is configured to receive gas measurements and to instruct a ventilation system of the vehicle to provide fresh air into the vehicle when a gas measurement indicates that a gas level exceeds a predefined gas level threshold.

9. The monitor according to claim 6, wherein the processor is configured to receive ultra violet radiation measurements and to instruct a window controller of the vehicle to close a window of the vehicle when an ultra violet radiation measurement indicates that a level of ultra violet radiation exceeds a predefined ultra violet level threshold.

10. The monitor according to claim 1, wherein the generating of the audio alert comprises playing music.

11. The monitor according to claim 1, wherein the generating of the audio alert comprises playing a speech.

12. The monitor according to claim 1, wherein the processor is configured to detect a decreased awareness level of the driver and to determine an awaking action selected from a list consisting of: playing music, talking to the driver and activating a wake-up call.

13. The monitor according to claim 1 comprising the alcohol sensor for detecting the alcohol level in the blood of the driver; wherein the processor is configured to prevent the ignition of the vehicle if the alcohol level in the blood of the driver exceeds the predefined alcohol level threshold.

14. The monitor according to claim 13, comprising the voice recognition sensor arranged to authenticate the driver that undergoes the alcohol level test.

15. The monitor according to claim 1, wherein the multiple sensors comprises: a one-lead ECG sensor, a heart rate sensor, an oxygen saturation sensor, a blood pressure sensor, a body temperature sensor, glucose meter, weight scale, environmental sensor and a breath sensor.

16. The monitor according to claim 1, wherein the multiple sensors comprises a one-lead ECG that comprises two electrodes coupled to the steering wheel; and wherein the display is configured to display an ECG graph when a one-lead ECG test is performed and to display a message that requires a confirmation to send one-lead ECG test results to the remote assistance site.

17. The monitor according to claim 1, wherein the vehicle elements are selected from a steering wheel of the vehicle and a seatbelt of the driver.

18. The monitor according to claim 1, comprising a smell detector arranged to detect a smell that differs from a predefined set of desired smells.

19. The monitor according to claim 1, wherein the selected action is selected out of opening a window of the vehicle, closing a window of the vehicle, changing a parameter of an air conditioning system, allowing an automatic driver to assume control of the vehicle, and generating a nerve stimulation.

20. The monitor according to claim 1, wherein the selected action comprises generating a nerve stimulation.

21. The monitor according to claim 1, wherein the monitor is arranged to detect the "leaving a person or an animal in a closed vehicle" situation; and trigger the selected action selected out of the opening of the window of the vehicle, sending the audio alert, sending the message to the third entity that indicates of the potential "leaving a person or animal in a closed vehicle" situation.

22. The monitor according to claim 21, wherein the monitor is arranged to determine the amount of opening based on the response of the person or animal that are positioned in the vehicle to the previous attempt to open the window of the vehicle.

23. The monitor according to claim 1, wherein the monitor is arranged to alter at least one parameter of the alert during an existence of the "leaving a person or animal in a closed vehicle" situation.

24. The monitor according to claim 1, comprising the radar that is arranged to monitor the driver and to provide the indication, in case of the accident, of fluid in lungs of the driver.

25. A method for monitoring a stress level of a driver of a vehicle, the method comprises:
receiving physiological information indicative of a stress level of the driver, from at least one sensor that is located within the vehicle and in a vicinity of the driver; wherein the at least one sensor comprises an ultra wide band radar;

detecting a stress level of the driver based on the physiological information, stored physiological information history and at least one predefined measurement threshold;

determining to initiate a stress level reduction action when a difference between at least one measurement of the physiological information and an average of associated stored measurements exceeds a predefined measurement change threshold;

performing, based on the determination, the stress level reduction action while the driver is within the vehicle, wherein the stress level reduction action is selected out of playing a relaxing music and activating a neck or back massage.

26. The method according to claim 25, wherein the at least one sensor is selected from a list consisting of: a heart rate sensor, a blood pressure sensor and a breath sensor.

27. The method according to claim 25 wherein the ultra wide band radar is located at a ceiling of the vehicle.

28. The method according to claim 25, comprising detecting, by a smell detector, a smell that differs from a predefined set of desired smells.

29. The method according to claim 25, wherein the stress level reduction is selected out of changing a parameter of an air conditioning system, allowing an automatic driver to assume control of the vehicle, and generating a nerve stimulation.

30. A method for monitoring an awareness state of a driver, comprising:

receiving physiological information indicative of an awareness level of a driver, from at least one sensor that is located in a vicinity of a driver; wherein the at least one sensor comprises an ultra wide band radar;

detecting the awareness level of the driver based on the physiological information, stored physiological information history and predefined measurements thresholds;

determining to initiate the awaking action when a difference between at least one measurement of the physiological information and an average of associated stored measurements exceeds a predefined measurement change threshold;

performing, based on the determination, the awaking action while the driver is within the vehicle, wherein the awaking action is selected from a list consisting of: playing a music, playing a speech and playing a sound.

31. The method according to claim 30, wherein the at least one sensor is selected from a list consisting of: a heart rate sensor, a blood pressure sensor and a breath sensor.

32. The method according to claim 30 wherein the ultra wide band radar is located at a ceiling of the vehicle.

33. A method for monitoring a driver of a vehicle, the method comprises:

receiving physiological information relating to the driver from at least one sensor;

detecting, based on the physiological information, a health problem of the driver, an awareness level of the driver and a stress level of the driver; wherein the detecting of the health problem of the driver differs from measuring an alcohol level in a blood of the driver;

determining a selected action to be performed based on the detection, wherein the action is selected from a list consisting of: establishing a call to a remote assistance site, transmitting the physiological information to a remote assistance site, generating an audio alert and generating a visual alert; and performing the selected action;

wherein the method further comprises at least one of the following:

(a) storing a history of the information of the driver (b) receiving ultra violet radiation measurements and instructing a window controller of the vehicle to close a window of the vehicle when an ultra violet radiation measurement indicates that a level of ultra violet radiation exceeds a predefined ultra violet level threshold;

(c) detecting a "leaving a person or an animal in a closed vehicle" situation; and triggering a selected action selected out of an opening of the window of the vehicle, sending an audio alert, sending a message to a third entity that indicates of a potential "leaving a person or animal in a closed vehicle" situation; and (d) monitoring, by a radar, the driver and providing an indication, in case of an accident, of fluid in lungs of the driver.

34. The method according to claim 33, wherein the performing of the selected action comprises establishing a call to the remote assistance site and transmitting the physiological information to the remote assistance site.

35. The method according to claim 33, further comprises storing the history of the physiological information of the driver.

36. The method according to claim 33, wherein the performing of the selected action comprises displaying video during a video conference call between the driver and the remote assistance site.

37. The method according to claim 33, wherein the performing of the selected action comprises displaying the visual alert and displaying visual content that is indicative of the physiological information.

38. The method according to claim 33, wherein the at least one sensor is selected from a list consisting of: a one-lead ECG, a heart rate sensor, an oxygen saturation sensor, a blood pressure sensor, a body temperature sensor, and a breath sensor.

39. The method according to claim 33, comprises receiving gas measurements and instructing a ventilation system of the vehicle to provide fresh air into the vehicle when a gas measurement indicates that a gas level exceeds a predefined gas level threshold.

40. The method according to claim 33, comprises receiving ultra violet radiation measurements and instructing the window controller of the vehicle to close the window of the vehicle when the ultra violet radiation measurement indicates that the level of ultra violet radiation exceeds the predefined ultra violet level threshold.

41. The method according to claim 33, wherein the generating of the audio alert comprises playing music.

42. The method according to claim 33, wherein the generating of the audio alert comprises playing a speech.

43. The method according to claim 33, comprising detecting a decreased awareness level of the driver and determining an awaking action selected from a list consisting of: playing music, talking to the driver and activating a wake-up call.

44. The method according to claim 33 comprises detecting an alcohol level in a blood of the driver and preventing an ignition of the vehicle if the alcohol level in the blood of the driver exceeds a predefined alcohol level threshold.

45. The method according to claim 33, comprising detecting the "leaving a person or an animal in a closed vehicle" situation; and triggering the selected action selected out of the opening of the window of the vehicle, sending the audio alert, sending the message to the third entity that indicates of the potential "leaving a person or animal in a closed vehicle" situation.

46. The method according to claim 45, comprising determining an amount of opening based on a response of the person or animal positioned in the vehicle to a previous attempt to open the window of the vehicle.

47. The method according to claim 45, comprising altering at least one parameter of the alert during an existence of the "leaving a person or animal in a closed vehicle" situation.

48. The method according to claim 33 comprising monitoring, by the radar, the driver and providing the indication, in case of the accident, of fluid in lungs of the driver.

* * * * *